United States Patent
Silvertand

(10) Patent No.: US 10,709,102 B2
(45) Date of Patent: Jul. 14, 2020

(54) TOMATO VARIETY NUN 09194 TOF

(71) Applicant: Nunhems B.V., Nunhem (NL)

(72) Inventor: Bernard Catharina Hubert Silvertand, Nunhem (NL)

(73) Assignee: NUNHEMS B.V., Nunhem (NL)

( * ) Notice: Subject to any disclaimer, the term of this patent is extended or adjusted under 35 U.S.C. 154(b) by 36 days.

(21) Appl. No.: 15/995,874

(22) Filed: Jun. 1, 2018

(65) Prior Publication Data

US 2018/0271044 A1    Sep. 27, 2018

Related U.S. Application Data

(60) Provisional application No. 62/513,466, filed on Jun. 1, 2017.

(51) Int. Cl.
| | |
|---|---|
| *A01H 5/08* | (2018.01) |
| *A01H 1/00* | (2006.01) |
| *A01H 6/82* | (2018.01) |

(52) U.S. Cl.
CPC ............... *A01H 6/825* (2018.05); *A01H 1/00* (2013.01); *A01H 5/08* (2013.01)

(58) Field of Classification Search
None
See application file for complete search history.

(56) References Cited

U.S. PATENT DOCUMENTS

| | | |
|---|---|---|
| 4,822,949 A | 4/1989 | Niego et al. |
| 5,349,128 A | 9/1994 | Quemada et al. |
| 5,492,827 A | 2/1996 | Dirks |
| 6,084,152 A | 7/2000 | Kwak et al. |
| 6,765,130 B2 | 7/2004 | Taurick |
| 2016/0165827 A1* | 6/2016 | Bunn ............... A01G 22/00 800/260 |

FOREIGN PATENT DOCUMENTS

| | | |
|---|---|---|
| WO | 2013182646 A1 | 12/2013 |
| WO | 2014076249 A1 | 5/2014 |
| WO | 2016120438 A1 | 8/2016 |
| WO | 2016207432 A1 | 12/2016 |

OTHER PUBLICATIONS

Colijn-Hooymans et al., "Competence for Regeneration of Cucumber Cotyledons is Restricted to Specific Developmental Stages," Plant Cell, Tissue and Organ Culture 39: 211-217, 1994.
Ince et al., "Genetic Relationships Within and Between Capsicum Species," Biochem Genet 48:83-95, 2010.
Pisanu et al., "Yield and Biometric Characteristics of 9 Clones Selected from the Population of "Spinoso Sardo" Artichokes," Acta Hort. 660, ISHS 2004.
Sang-Gu et al., "Callus Growth and Plant Regeneration in Diverse Cultivars of Cucumber (*Cucumis sativus* L.)," Plant cell, Tissue and Organ Culture 12: 67-74, 1988.
Vidaysky & Czosnek, "Tomato Breeding Lines Resistant and Tolerant to Tomato Yell Leaf Curl Virus Issued from Lycopersicon Hirsutum," Phytopathology 88(9): 910-914, 1988.
Vos et al., "AFLP: A New Technique for DNA Fingerprinting," Nucleic Acid Research vol. 23, No. 21, pp. 4407-4414, 1995.
Wijnker et al., "Hybrid Recreation by Reverse Breeding in *Arabidopsis thaliana*," Nature Protocols vol. 9, No. 4, pp. 761-772, 2014.
"Objective Description of Variety, Tomato (*Lycopersicon esculentum* Mill.)," U.S. Department of Agriculture, Aricultural Marketing Service, Science and Technology, Plant Variety Protection Office, http://www.ams.usda.gov/AMSv1.0/getfile?dDocName=STELDEV3002687, Jun. 2015.
"Guidelines for the Conduct of Tests for Distinctness, Uniformity and Stability," International Union for the Protection of New Varieties of Plants (UPOV) http://www.upov.int/en/publications/tg-rom/tg061/tg_61_7.pdf, Apr. 4, 2001.

* cited by examiner

*Primary Examiner* — Phuong T Bui
(74) *Attorney, Agent, or Firm* — Arent Fox LLP

(57) ABSTRACT

The disclosure provides hybrid variety of tomato, NUN 09194 TOF as well as seeds and plants and fruits thereof.

22 Claims, No Drawings

TOMATO VARIETY NUN 09194 TOF

CROSS-REFERENCE TO RELATED APPLICATIONS

This application claims the benefit of U.S. Patent Application Ser. No. 62/513,466, filed Jun. 1, 2017, which is incorporated herein by reference in its entirety.

FIELD OF THE INVENTION

The disclosure relates to the field of plant breeding and, more specifically, to the tomato variety NUN 09194 TOF. The disclosure further relates to vegetative reproductions of NUN 09194 TOF, methods for tissue culture of NUN 09194 TOF, methods for regenerating a plant from such a tissue culture and to phenotypic variants of NUN 09194 TOF.

BACKGROUND

The goal of plant breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties. Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding, and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

Tomato (*Solanum lycopersicum* and closely related species) is naturally a diploid and the basic chromosome number of the genus is x=12, most are 2n=2x=24, including the cultivated ones. It originated in the New World and has since become a mayor food crop. In 2012, FAOSTAT estimated world production at over 160 million ton.

Tomato cultivars may be grouped by maturity, i.e., the time required from planting the seed to the stage where fruit harvest can occur. Standard maturity classifications include 'early', 'midseason' or 'late-maturing'. Another classification for tomatoes is the developmental timing of fruit set. 'Determinate' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange, brown and purple. Additionally, there are multi-colored varieties exemplified by mainly red fruited varieties with green shoulders, and both striped- and variegated-colored fruit. Tomatoes can also be classified by their market. Some varieties are intended for fresh consumption by consumers. These tomatoes require, for example, good storage properties. Other tomato varieties are optimized for the processing industry. Processing tomatoes can be canned whole, canned, diced or chopped, dried, roasted, pasted, puréed or concentrated, juiced, frozen, or put into ready-made dishes, for example sauces, stews or soups. The fruits of tomato plants which are more suitable for processing are generally red colored and have pink to red/crimson fruit flesh.

SUMMARY OF VARIOUS EMBODIMENTS OF THE INVENTION

The disclosure provides for tomato variety NUN 09194 TOF, products thereof, and methods of using the same. NUN 09194 TOF is a big cluster tomato suitable for fresh consumption, and preferably grown in a glasshouse.

In one aspect, the disclosure provides a seed of tomato variety NUN 09194 TOF, wherein a representative sample of said seed will be deposited under Accession Number NCIMB 43588. The disclosure also provides for a plurality of seeds of NUN 09194 TOF. The tomato seed of NUN 09194 TOF may be provided as an essentially homogeneous population of tomato seed. The population of seed of NUN 09194 TOF may be particularly defined as being essentially free from other seed. The seed population may be grown into plants to provide an essentially homogeneous population of tomato plants as described herein.

The disclosure also provides a plant grown from a seed of tomato variety NUN 09194 TOF and a plant part thereof. In another aspect, the disclosure provides for a hybrid variety of tomato called NUN 09194 TOF. The disclosure also provides for a progeny of NUN 09194 TOF. In another aspect, the disclosure provides a plant or a progeny retaining all or all but one, two or three of the "distinguishing characteristics" or all or all but one, two or three of the "morphological and physiological characteristics" of NUN 09194 TOF and methods for producing that plant or progeny.

In one aspect, the disclosure provides a plant or a progeny having all the physiological and morphological characteristics of variety NUN 09194 TOF when grown under the same environmental conditions. In another aspect, the plant or progeny has all or all but one, two or three of the physiological and morphological characteristics of NUN 09194 TOF when measured under the same environmental conditions and evaluated at significance levels of 1%, 5% or 10% significance (which can also be expressed as a p-value), wherein a representative sample of seed of variety NUN 09194 TOF will be deposited under Accession Number NCIMB 43588. In another aspect, the plant or progeny has all or all but one, two or three of the physiological and morphological characteristics as listed in Table 1 and/or 2 for variety NUN 09194 TOF when measured under the same environmental conditions and evaluated at significance levels of 1%, 5% or 10% significance (which can also be expressed as a p-value).

In another aspect, a plant of NUN 09194 TOF or a progeny thereof has 7, 8, or more or all of the following distinguishing characteristics: 1) Typical fruit shape; 2) Average length of mature fruit; 3) Typical number of fruit locules; 4) Typical shape of mature fruit pistil scar; 5) Average plant height; 6) Average number of nodes between early inflorescences; 7) Typical leaf pubescence; 8) Average number of flowers in inflorescence; 9) Typical locular gel color of table-ripe fruit and 10) Typical epidermis color.

In other aspects, the disclosure provides for a plant part obtained from variety NUN 09194 TOF, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a scion, a stock, a rootstock, a pistil, an anther, or a flower or a part thereof. Fruits are particularly important plant parts. In another aspect, the plant part obtained from variety NUN 09194 TOF is a cell, optionally a cell in a cell or tissue culture. That cell may be grown into a plant of NUN 09194 TOF.

The disclosure also provides a cell culture of NUN 09194 TOF and a plant regenerated from NUN 09194 TOF, which plant has all the characteristics of NUN 09194 TOF, when grown under the same environmental conditions, as well as methods for regenerating NUN 09194 TOF. Alternatively, a regenerated plant may have one characteristic that is different from NUN 09194 TOF.

The disclosure further provides a vegetatively propagated plant of variety NUN 09194 TOF having all or all but one, two or three of the morphological and physiological characteristics of the variety disclosed herein when grown under the same environmental conditions.

The disclosure furthermore provides a tomato fruit produced on a plant grown from a seed of NUN 09194 TOF.

In another aspect, the disclosure provides a seed growing or grown on a plant of NUN 09194 TOF (i.e., produced after pollination of the flower of NUN 09194 TOF).

Definitions

"Tomato" refers herein to plants of the species *Solanum lycopersicum*, or a closely related species, and fruits thereof. *Solanum lycopersicum* is also known as *Lycopersicon lycopersicum* (L.) (H. Karst.), or *Lycopersicon esculentum* Mill. The most commonly eaten part of a tomato is the fruit or berry.

"Cultivated tomato" refers to plants of *Solanum lycopersicum*, or a closely related species, (e.g., varieties, breeding lines or cultivars of the species *S. lycopersicum* as well as crossbreds thereof, or crossbreds with other *Solanum* species), cultivated by humans and having good agronomic characteristics.

"Cluster tomato" refers to tomatoes that suitable for sale on a stem. The individual fruits on the cluster ripen together. They are typically consumed fresh.

The terms "tomato plant designated NUN 09194 TOF", "NUN 09194 TOF", "NUN 09194", "NUN 09194 F1", "09194 TOF" or "tomato 09194" are used interchangeably herein and refer to a tomato plant of variety NUN 09194 TOF, representative seed of which is to be deposited under Accession Number NCIMB 43588.

A "seed of NUN 09194 TOF" refers to a tomato seed which can be grown into a plant of NUN 09194 TOF wherein a representative sample of viable seed of NUN 09194 TOF is to be deposited under Accession Number NCIMB 43588. A seed can be in any stage of maturity, for example a mature, viable seed, or an immature, non-viable seed. A seed comprises an embryo and maternal tissues.

An "embryo of NUN 09194 TOF" refers to an "F1 hybrid embryo" as present in a seed of NUN 09194 TOF, a representative sample of said seed of NUN 09194 TOF to be deposited under Accession Number NCIMB 43588 .

A "seed grown on NUN 09194 TOF" refers to a seed grown on a mature plant of NUN 09194 TOF or inside a fruit of NUN 09194 TOF. The "seed grown on NUN 09194 TOF" contains tissues and DNA of the maternal parent, NUN 09194 TOF. The "seed grown on NUN 09194 TOF" contains an F2 embryo. When said seed is planted, it grows into a first generation progeny plant of NUN 09194 TOF.

A "fruit of NUN 09194 TOF" refers to a fruit containing maternal tissues of NUN 09194 TOF as will be deposited under Accession Number NCIMB 43588. The fruit comprises pericarp, septa, epidermis, columella, locular cavity, vascular bundles and optionally seed. Pericarp, septa, epidermis, columella, locular cavity, vascular bundles, and seedcoat of the seed are maternal tissues, e.g., they are genetically identical to the plant on which they grow. In one aspect, the fruit contains seed grown on NUN 09194 TOF. In another aspect, the fruit does not contain seed, i.e., the fruit is parthenocarpic. The skilled person is familiar with methods for inducing parthenocarpy. Those methods comprise chemically or genetically inducing parthenocarpy. Compounds suitable for chemically inducing parthenocarpy comprise auxins, gibberellins and cytokinins. Methods for genetically inducing parthenocarpy comprise the methods described in WO2008143504, WO1998/024301, WO1999/021411, WO2000/074468 and EP142842, which are herein incorporated by reference in their entirety.

An "essentially homogeneous population of tomato seed" is a population of seeds where at least 97%, 98%, 99% or more of the total population of seed are seed of NUN 09194 TOF.

An "essentially homogeneous population of tomato plants" is a population of plants where at least 97%, 98%, 99% or more of the total population of plants are plants of NUN 09194 TOF.

The phrase "essentially free from other seed" refers to a population of seed where less than 3%, 2%, 1% or less of the total population of seed is seed that is not a tomato seed or, in another aspect, less than 3%, 2%, 1% or less of the total population of seed is seed that is not seed of NUN 09194 TOF.

"Tissue culture" or "cell culture" refers to a composition comprising isolated cells of the same or a different type or a collection of such cells organized into parts of a plant. Tissue culture of various tissues of tomato and regeneration of plants therefrom is well known and widely published (see, e.g., Bhatia et al. (2004), Plant Cell, Tissue and Organ Culture 78: 1-21. Similarly, methods of preparing cell cultures are known in the art.

"UPOV descriptors" are the plant variety descriptors described for tomato in the "Guidelines for the Conduct of Tests for Distinctness, Uniformity and Stability, TG/44/10 (Geneva 2011, revised 2013), as published by UPOV (International Union for the Protection of New Varieties and Plants, available on the world wide web at upov.int) and which can be downloaded from the world wide web at upov.int/edocs/tgdocs/en/tg044.pdf and is herein incorporated by reference in its entirety "USDA descriptors" are the plant variety descriptors for tomato (Solanum lycopersicum or Lycopersicon esculentum Mill.) as published by the US Department of Agriculture, Agricultural Marketing Service, Plant Variety Protection Office, Beltsville, Md. 20705 (available on the world wide web at ams.usda.gov) and which can be downloaded from the world wide web at ams.usda.gov/sites/default/files/media/55-Tomato %20ST-470-55%202015.pdf "Non-USDA descriptors" are other descriptors suitable for describing tomato.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticulwral Society, charity No: 222879, PO Box 313 London SW1P2PE.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, hypocotyl, cotyledon, a scion, a graft, a stock, a rootstock, a pistil, an anther, and a flower or parts of any of these and the like. Seed can be mature or immature. Pollen or ovules may be viable or non-viable. Also any developmental stage is included, such as seedlings, cuttings prior or after rooting, mature plants or leaves. Alternatively, a plant part may also include a plant seed which comprises one or two sets of chromosomes derived from the parent plant, e.g., from NUN 09194 TOF. An F2 progeny produced from self-pollination of NUN 09194 TOF will thus comprise two sets of chromosomes derived from NUN 09194 TOF, while an F2 progeny derived from cross-fertilization of NUN 09194 TOF will comprise only one set of chromosomes from NUN 09194 TOF, and the other set of chromosomes from the other parent.

"Harvested plant material" refers herein to plant parts (e.g., single fruits or clusters of fruits detached from the whole plant), which have been collected for further storage and/or further use.

"Reference Variety for NUN 09194 TOF" refers herein to variety Merlice, a commercial variety from company Seminis, which has been planted in a trial together with NUN 09194 TOF. USDA descriptors of NUN 09194 TOF were compared to the USDA descriptors of Merlice.

"Rootstock" or "stock" refers to the plant selected for its roots, in particular for the resistance of the roots to diseases or stress (e.g., heat, cold, salinity etc.). Normally the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired tomato fruit.

"Stock/scion" or grafted plant refers to a tomato plant comprising a rootstock from one plant grafted to a scion from another plant.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 09194 TOF may have one or more (or all) of the essential physiological and/or morphological characteristics of said variety listed in Table 1 and/or 2, as determined at the 5% significance level (i.e., $p<0.05$) when grown under the same environmental conditions.

"Distinguishing characteristics" or "distinguishing morphological and/or physiological characteristics" refers herein to the characteristics which distinguish (i.e., are different) between the new variety and other tomato varieties, such as the Reference Variety, when grown under the same environmental conditions. The distinguishing characteristics between NUN 09194 TOF and Reference Variety are described herein and also can be seen in Table 1 and/or Table 2. When comparing NUN 09194 TOF with different varieties, the distinguishing characteristics will be different. In one aspect, the distinguishing characteristics may therefore include at least one, two, three or more (or all) of the characteristics listed in Table 1 and/or 2. All numerical distinguishing characteristics are statistically significantly different at $p<0.05$ between NUN 09194 TOF, and the other variety, e.g., Reference Variety.

NUN 09194 TOF has the following distinguishing characteristics when compared to the Reference Variety: 1) Typical fruit shape; 2) Average length of mature fruit; 3) Typical number of fruit locules; 4) Typical shape of mature fruit pistil scar; 5) Average plant height; 6) Average number of nodes between early inflorescences; 7) Typical leaf pubescence; 8) Average number of flowers in inflorescence; 9) Typical locular gel color of table-ripe fruit and 10) Typical epidermis color. This can be seen in Table 1, where the USDA characteristics of NUN 09194 TOF are compared to the characteristics of the Reference Variety, when grown under the same environmental conditions.

Thus, a tomato plant "comprising the distinguishing characteristics of NUN 09194 TOF (such as a progeny plant) refers herein to a plant which does not differ significantly from said variety in the distinguishing characteristics above. Therefore, in one aspect, a plant (such as a progeny plant of NUN 09194 TOF) is provided which does not differ significantly from NUN 09194 TOF in the distinguishing characteristics above.

Similarity and differences between two different plant lines or varieties can be determined by comparing the number of morphological and/or physiological characteristics (e.g., the characteristics as listed in Table 1 and/or 2) that are the same (i.e., statistically not significantly different) or that are different (i.e., statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

A "plant line" is, for example, a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all tomato fruits harvested per hectare of a particular line or variety. It is understood that "yield" expressed as weight of all tomato fruits harvested per hectare can be obtained by multiplying the number of plants per hectare times the "yield per plant". "Marketable yield" means the total weight of all marketable tomato fruits, especially fruit which is not cracked, damaged or diseased, harvested per hectare of a particular line or variety. A "marketable fruit" is a fruit that has commercial value.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Harvest maturity" is referred to as the stage at which a tomato fruit is ripe or ready for harvest or the optimal time to harvest the fruit for the market, for processing or for consumption. In one aspect, harvest maturity is the stage which allows proper completion of the normal ripening.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one tomato line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 09194 TOF. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another tomato plant of the same variety or another variety or line, or with wild tomato plants. A progeny may comprise a mutation or a transgene. A "first generation progeny" or is the progeny directly derived from, obtained from, obtainable from or derivable from the parent plant by, e.g., traditional breeding methods (selfing and/or cross-pollinating) or regeneration. Thus, a plant of NUN 09194 TOF is the male parent, the female parent or both of a first generation progeny of that variety. Progeny may have all the physiological and morphological characteristics of NUN 09194 TOF when grown under the same environmental conditions and/or progeny may have (be selected for having) one or more of the distinguishing characteristics of tomato described herein. Using common breeding methods such as backcrossing or recurrent selection, one or more specific characteristics may be introduced into said variety, to provide or a plant comprising all but 1, 2, or 3 or more of the morphological and physiological characteristics of NUN 09194 TOF (as listed in Table 1 and/or 2)

The terms "gene converted" or "conversion plant" or "single locus converted plant" in this context refer to tomato plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise, a "Single Locus Converted (Conversion) Plant" refers to plants developed by plant breeding techniques comprising or consisting of mutation and/or by genetic transformation and/or by backcrossing, wherein essentially all of the desired morphological and physiological characteristics of a tomato variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for tomatoes described herein. The mean, if not indicated otherwise within this application, refers to the arithmetic mean of measurements on at least 10 different, randomly selected plants of a variety or line.

DETAILED DESCRIPTION OF VARIOUS EMBODIMENTS OF THE INVENTION

The disclosure relates to a plant of NUN 09194 TOF, wherein a representative sample of seeds of said variety will be deposited under the Budapest Treaty, with Accession number NCIMB 43588. NUN 09194 TOF is a big cluster tomato suitable for fresh consumption, and preferably grown in a glasshouse.

The disclosure also relates to a seed of tomato variety, referred to as NUN 09194 TOF, wherein a representative sample of said seed will be deposited under the Budapest Treaty, with Accession number NCIMB 43588.

In another aspect, the disclosure provides for a plant part of variety NUN 09194 TOF, preferably a fruit, a representative sample of seed from said variety to be deposited under the Budapest Treaty, with Accession number NCIMB 43588.

A seed of hybrid variety NUN 09194 TOF is obtainable by crossing the male parent of said variety with the female parent of said variety and harvesting the seeds produced on the female parent. The resultant seeds of said variety can be grown to produce plants of said variety. In one aspect, a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 09194 TOF.

Also provided is a plant of tomato variety NUN 09194 TOF, or a fruit or other plant part thereof, produced from a seed, wherein a representative sample of said seeds to be deposited under the Budapest Treaty, with Accession Number NCIMB 43588.

Also provided is a plant part obtained from variety NUN 09194 TOF, wherein said plant part: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, hypocotyl, cotyledon, a scion, a stock, a rootstock, a pistil, an anther, and a flower or a part thereof. Fruits are particularly important plant parts. Fruits may be parthenocarpic, or seedless, or contain immature and/or nonviable seeds. In a further aspect, the plant part obtained from variety NUN 09194 TOF is a cell, optionally a cell in a cell or tissue culture. That cell may be grown into a plant of NUN 09194 TOF. A part of NUN 09194 TOF (or of progeny of that variety or of a plant having all physiological and/or morphological characteristics but one, two or three which are different from those of NUN 09194 TOF) further encompasses any cells, tissues, or organs obtainable from the seedlings or plants in any stage of maturity.

The disclosure also provides for a food or feed product or a processed product comprising or consisting of a plant part described herein. Preferably, the plant part is a tomato fruit or part thereof and/or an extract from a fruit or another plant part described herein comprising at least one cell of NUN 09194 TOF. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 09194 TOF can be stored and/or processed further. The disclosure thus also provides for a food or feed product comprising one or more of such parts, such as canned, chopped, cooked, roasted, in a sauce, in a sandwich, pasted, puréed or concentrated, juiced, frozen, dried, pickled, or powdered tomato fruit from NUN 09194 TOF or from progeny of said variety, or from a derived variety, such as a plant having all but one, two or three physiological and/or morphological characteristics of NUN 09194 TOF.

In another aspect, the disclosure provides for a tomato fruit of variety NUN 09194 TOF, or a part of a fruit of said variety. The fruit can be in any stage of maturity, for example immature or mature. In another aspect, the disclosure provides for a container comprising or consisting of a plurality of harvested tomato fruits or parts of fruits of said variety, or fruits of progeny thereof, or fruits of a derived variety.

In another aspect, the plant, plant part or seed (fresh and/or processed) of NUN 09194 TOF is inside one or more containers, such as cans, boxes, crates, bags, cartons, Modified Atmosphere Packaging, films (e.g., biodegradable films), etc. In a particular aspect, the container comprises a plurality of seeds of NUN 09194 TOF, or a plurality of plant parts of NUN 09194 TOF.

The disclosure further relates to a tomato variety, referred to as NUN 09194 TOF, which—when compared to its REFERENCE VARIETY Merlice—has the following distinguishing characteristics: 1) Typical fruit shape; 2) Average length of mature fruit; 3) Typical number of fruit locules; 4) Typical shape of mature fruit pistil scar; 5) Average plant height; 6) Average number of nodes between early inflorescences; 7) Typical leaf pubescence; 8) Average number of flowers in inflorescence; 9) Typical locular gel color of table-ripe fruit and 10) Typical epidermis color, where the characteristics are determined at the 5% significance level for plants grown under the same environmental conditions. Also encompassed are parts of that plant.

In one aspect, a plant of NUN 09194 TOF or a progeny plant thereof, comprises all of the following morphological and/or physiological characteristics (i.e., average values of distinguishing characteristics, as indicated on the USDA Objective description of variety—tomato (unless indicated otherwise)): 1) Typical fruit shape; 2) Average length of mature fruit; 3) Typical number of fruit locules; 4) Typical shape of mature fruit pistil scar; 5) Average plant height; 6) Average number of nodes between early inflorescences; 7) Typical leaf pubescence; 8) Average number of flowers in inflorescence; 9) Typical locular gel color of table-ripe fruit and 10) Typical epidermis color, where the characteristics are determined at the 5% significance level for plants grown under the same environmental conditions. An example of values for the distinguishing characteristics collected in a trial run according to UDSA requirements can be found in Table 1. A part of this plant is also provided.

NUN 09194 TOF may further exhibit may further exhibit one or more of the following traits: a) Average internode length after $2^{nd}$ inflorescence, and/or b) Average number of locules.

In another aspect, NUN 09194 TOF has resistance to *Verticillium dahlia* (Va and Vd) that is 9 (present), resistance to *Fusarium oxysporum* f. sp. *lycopersici* (Fol) race 0, and 1 that is 9 (present), resistance to *Fusarium oxysporum* f. sp. *radicis lycopersici* (Forl) that is 9 (present), resistance to *Fulvia fulvia* f (Ff) group A, B, C, D, and E that is 9 (present), resistance to Tomato Mosaic Virus (ToMV) strain 0, strain 1 and strain 2 that is 9 (present), and resistance to *Oidium neolycopersici* (On) that is 9 (present).

The disclosure further provides a tomato plant which does not differ from the physiological and morphological characteristics of the plant of NUN 09194 TOF as determined at the 1%, 2%, 3%, 4% or 5% significance level when grown under the same environmental conditions. In a particular aspect, the plants are measured in the same trial (e.g., the trial is conducted as recommended by USDA or UPOV). The disclosure also comprises a part of said plant The disclosure also provides a tissue or cell culture comprising cells of NUN 09194 TOF. Such a tissue culture can, for example, be grown on plates or in liquid culture, or be frozen for long term storage. The cells of NUN 09194 TOF used to start the culture can be selected from any plant part suitable for vegetative reproduction, or in a particular aspect, can be one or more of an embryo, meristem, a cotyledon, a hypocotyl, pollen, a leaf, an anther, a root, a root tip, a pistil, a petiole, a flower, a fruit, seed, and/or a stem of NUN 09194 TOF. In another particular aspect, the tissue culture does not contain somaclonal variation or has reduced somaclonal variation. The skilled person is familiar with methods to reduce or prevent somaclonal variation, including regular reinitiation.

In one aspect, the disclosure provides a tomato plant regenerated from the tissue or cell culture of NUN 09194 TOF, wherein the regenerated plant is not significantly different from NUN 09194 TOF in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another aspect, the disclosure provides a tomato plant regenerated from the tissue or cell culture of NUN 09194 TOF, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A tomato described herein, such as NUN 09194 TOF, or its progeny, or a plant having all physiological and/or morphological characteristics but one, two or three which are different from those of NUN 09194 TOF, can also be reproduced using vegetative reproduction methods. Therefore, the disclosure provides for a method of producing a plant, or a part thereof, of variety NUN 09194 TOF, comprising vegetative propagation of said variety. Vegetative propagation comprises regenerating a whole plant from a plant part of variety NUN 09194 TOF, (or from a progeny of said variety or from or a plant having all physiological and/or morphological characteristics of said variety but one, two or three different characteristics), such as a cutting, a cell culture or a tissue culture.

The disclosure also provides methods of vegetatively propagating a part of the plant of the disclosure NUN 09194 TOF. In certain aspects, the method comprises: (a) collecting tissue or cells capable of being propagated from a plant described herein; (b) cultivating said tissue or cells to obtain proliferated shoots; and (c) rooting said proliferated shoots, to obtain rooted plantlets. Steps (b) and (c) may also be reversed, i.e., first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 09194 TOF. In a particular aspect, the part of the plant to be propagated is a cutting, a cell culture or a tissue culture.

The disclosure also provides for a vegetatively propagated plant of variety NUN 09194 TOF (or from progeny of said variety or from or a plant having all but one, two or three physiological and/or morphological characteristics of that variety), wherein the plant has all of the morphological and physiological characteristics of NUN 09194 TOF, when the characteristics are determined at the 5% significance level for plants grown under the same conditions. In another aspect, the propagated plant has all but one, two or three of the morphological and physiological characteristics of NUN 09194 TOF, when the characteristics are determined at the 5% significance level for plants grown under the same conditions. A part of said propagated plant or said propagated plant with one, two or three differences is also included.

In another aspect, the disclosure provides a method for producing a tomato plant part, preferably a fruit, comprising: growing a plant of NUN 09194 TOF until it sets at least one fruit, and collecting the fruit. Preferably, the fruit is collected at harvest maturity. In another embodiment, the fruit is collected when the seed is ripe. A plant of NUN 09194 TOF can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop. Tomato can also be grown entirely in greenhouses.

In still another aspect, the disclosure provides a method of producing a tomato plant, comprising crossing a plant of tomato NUN 09194 TOF with a second tomato plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent tomato plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect, the disclosure provides a method of producing a plant, comprising selfing a plant of variety NUN 09194 TOF one or more times, and selecting a progeny plant from said selfing. In one aspect, the progeny plant retains all the distinguishing characteristics of NUN 09194 TOF described above. In a different aspect, the progeny plant comprises all (or all but one, two or three) of the physiological and morphological characteristic of NUN 09194 TOF of Table 1, and/or Table 2. In a further aspect, the progeny plant comprises all physiological and morphological characteristic of NUN 09194 TOF when grown under the same environmental conditions.

In other aspects, the disclosure provides a progeny plant of variety NUN 09194 TOF such as a progeny plant obtained by further breeding that variety. Further breeding with the variety includes selfing that variety one or more times and/or cross-pollinating that variety with another tomato plant or variety one or more times. In particular, the disclosure provides for a progeny plant that retains all the essential morphological and physiological characteristics of NUN 09194 TOF or, in another aspect, a progeny plant that retains all, or all but one, two or three, of the morphological and physiological characteristics of NUN 09194 TOF, optionally all or all but one, two or three of the characteristics as listed in Table 1 and/or 2, when grown under the same environmental conditions, determined at the 5% significance level for numerical characteristics. In a particular aspect, the progeny is a first generation progeny, i.e., the ovule or the pollen (or both) used in the crossing is an ovule or pollen of variety NUN 09194 TOF, where the pollen comes from an anther and the ovule comes from an ovary of NUN 09194 TOF. In another aspect, the disclosure provides for a vegetative reproduction of the variety and a plant having all, or all but 1, 2, or 3 of the physiological and morphological characteristics of NUN 09194 TOF (e.g., as listed in Table 1 and/or 2).

The disclosure also provides a method for collecting pollen of NUN 09194 TOF, comprising collecting pollen from a plant of NUN 09194 TOF. Alternatively, the method comprises growing a plant of NUN 09194 TOF until at least one flower contains pollen and collecting the pollen.

Preferably, the pollen is collected when it is mature or ripe. A suitable method for collecting pollen comprises collecting anthers or the part of the anther that contains pollen, for example by cutting the anther or the part of the anther off. Pollen can be collected in a container. Optionally, collected pollen can be used to pollinate a tomato flower.

The morphological and/or physiological differences between two different individual plants described herein (e.g., between NUN 09194 TOF and a progeny of NUN 09194 TOF) or between a plant of NUN 09194 TOF or progeny of said variety, or a plant having all, or all but 1, 2, or 3, of the physiological and morphological characteristics of NUN 09194 TOF (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said tomato cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of tomato. Thus, the disclosure comprises tomato plant having one, two or three physiological and/or morphological characteristics which are different from those of the plant of NUN 09194 TOF and which otherwise has all the physiological and morphological characteristics of the plant of NUN 09194 TOF, when determined at the 5% significance level for plants grown under the same environmental conditions. In another aspect, embodiment, the different characteristic is affected by a mutation, optionally induced mutation, or by transformation.

The morphological and physiological characteristics (and the distinguishing characteristics) of NUN 09194 TOF are provided in the Examples, in Table 1 and/or 2. Encompassed herein is also a plant obtainable from NUN 09194 TOF (e.g., by selfing and/or crossing and/or backcrossing with said variety and/or progeny of said variety) comprising all or all but one, two or three of the physiological and morphological characteristics of NUN 09194 TOF listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society (RHS) Chart.

In yet a further aspect, the disclosure provides for a method of producing a new tomato plant. The method comprises crossing NUN 09194 TOF, or a plant comprising all but 1, 2, or 3 of the morphological and physiological characteristics of NUN 09194 TOF (as listed in Table 1 and/or 2), or a progeny plant thereof, either as male or as female parent, with a second tomato plant (or a wild relative of tomato) one or more times, and/or selfing a tomato plant of NUN 09194 TOF, or a progeny plant thereof, one or more times, and selecting progeny from said crossing and/or selfing. The second tomato plant may for example be a line or variety of the species Solanum lycopersicon, S. chilense, S. habrochaites, S. penelli, S. peruvianum, S. pimpinellifolium or other Solanum species.

The disclosure provides for methods of producing plants which retain all the morphological and physiological characteristics of a plant described herein. The disclosure provides also for methods of producing a plant comprising all but 1, 2, or 3 or more of the morphological and physiological characteristics of NUN 09194 TOF (e.g., as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 09194 TOF if its DNA fingerprint is at least 80%, 90%, 95% or 98% identical to the fingerprint of that variety. In a particular aspect, AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Ince et al., (2010) Biochem. Genet. 48:83-95).

The disclosure also provides a plant and a variety obtained or selected by applying these methods on NUN 09194 TOF. Such a plant may be produced by crossing and/or selfing, or alternatively, a plant may simply be identified and selected amongst plants of said variety, or progeny of said variety, e.g., by identifying a variant within NUN 09194 TOF or within progeny of said variety (e.g., produced by selfing) which variant differs from the variety described herein in one, two or three of the morphological and/or physiological characteristics (e.g., in one, two or three distinguishing characteristics), e.g., those listed in Table 1 and/or 2 or others. In one aspect, the disclosure provides a tomato plant having a Jaccard's Similarity index with NUN 09194 TOF of at least 0.8, e.g., at least 0.85, 0.9, 0.95, 0.98 or even at least 0.99.

In some aspects, the disclosure provides a tomato plant comprising genomic DNA having at least 95%, 96%, 97%, 98% or 99% sequence identity compared to the genomic DNA sequence of a plant of NUN 09194 TOF as deposited under Accession Number NCIMB 43588. In some aspects, the tomato plant further comprises all or all but 1, 2, or 3 of the morphological and physiological characteristics of NUN 09194 TOF (e.g., as listed in Table 1 and/or 2). In other aspects, the tomato plant is a hybrid or other derived from a seed or plant of NUN 09194 TOF. In other aspects, the tomato plant comprises the distinguishing characteristics of NUN 09194 TOF.

For the purpose of this disclosure, the "sequence identity" of nucleotide sequences, expressed as a percentage, refers to the number of positions in the two optimally aligned sequences which have identical residues (×100) divided by the number of positions compared. A gap, i.e., a position in the pairwise alignment where a residue is present in one sequence but not in the other, is regarded as a position with non-identical residues. A pairwise global sequence alignment of two nucleotide sequences is found by aligning the two sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (EMBOSS, Rice et al., Trends in Genetics June 2000, vol. 16, No. 6. pp. 276-277).

The disclosure also provides methods for determining the identity of parental lines of plants described herein, in particular the identity of the female line. WO2013/182646, which is hereby incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of a plant of NUN 09194 TOF or is a progeny of said variety, because the seed coat of the seed is a maternal tissue genetically identical to said variety. In one aspect, the disclosure relates to a tomato seed comprising maternal tissue of NUN 09194 TOF. In another aspect, the disclosure relates to a tomato seed comprising a maternal tissue of NUN 09194 TOF. In another particular aspect, the disclosure provides for a method of identifying the female parental line of NUN 09194 TOF by analyzing the seed coat of a seed of that variety, In another aspect, the disclosure provides for a method of determining whether a seed is grown on NUN 09194 TOF by analyzing the seed coat or another maternal tissue of said seed.

By crossing and/or selfing, (one or more) single traits may be introduced into NUN 09194 TOF (e.g., using backcrossing breeding schemes), while retaining the remaining morphological and/or physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into NUN 09194 TOF by breeding with said variety.

Alternatively, a single trait converted plant or single locus converted plant of NUN 09194 TOF may be produced by (i) genetically transforming or mutating cells of NUN 09194 TOF; (ii) growing the cells into a plant; and (iii) optionally selecting a plant that contains the desired single locus conversion. The skilled person is familiar with various techniques for genetically transforming a single locus in a plant cell, or mutating said cells.

Any pest or disease resistance genes may be introduced into a plant NUN 09194 TOF, progeny of said variety or into a plant comprising all but 1, 2, or 3 or more of the morphological and physiological characteristics of NUN 09194 TOF (e.g., as listed in Table 1). Resistance to one or more of the following diseases or pests may be introduced into plants described herein: Tomato Mosaic Virus, Curly TOF Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), *Alternaria*, Bacterial Spot (*Xanthomonas vesicatoria*), Nematode (*Meloidogyne* spp), Late blight (*Phytophthora infestans* races), Leaf mold (*Cladosporium fulvum* races), Colorado potato beetle, Spider mites, Whitefly and/or *Verticillium* Wilt (*Verticillium dahliae*). Other resistance genes, against pathogenic viruses, fungi, bacteria, nematodes, insects or other pests may also be introduced.

The disclosure also provides a method for developing a tomato plant in a tomato breeding program, using a tomato plant described herein, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing NUN 09194 TOF or progeny of said variety, or a plant comprising all but 1, 2, or 3 or more of the morphological and physiological characteristics of NUN 09194 TOF (e.g., as listed in Table 1 and/or 2), with a different tomato plant, and wherein one or more offspring of the crossing are subject to one or more plant breeding techniques: recurrent selection, backcrossing, pedigree breeding, mass selection, mutation breeding and genetic marker enhanced selection (see e.g., Vidaysky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

The disclosure also provides a tomato plant comprising at least a first set of the chromosomes of tomato variety NUN 09194 TOF, a sample of seed of said variety to be deposited under Accession Number NCIMB 43588; optionally further comprising a single locus conversion or a mutation, wherein said plant has essentially all of the morphological and physiological characteristics of the plant comprising at least a first set of the chromosomes of said variety. In another aspect, this single locus conversion confers a trait wherein the trait is yield, storage properties, color, flavor, male sterility, herbicide tolerance, insect resistance, pest resistance, disease resistance, environmental stress tolerance, modified carbohydrate metabolism, modified protein metabolism and ripening or the mutation occurs in any of the following genes acs2, acs4, rin, pp2c1, arf9, intense, myb12.

In one aspect, a plant of NUN 09194 TOF may also be mutated (by e.g., irradiation, chemical mutagenesis, heat treatment, etc.) and mutated seeds or plants may be selected in order to change one or more characteristics of said variety. Methods such as TILLING may be applied to tomato populations in order to identify mutants. Similarly, NUN 09194 TOF may be transformed and regenerated, whereby one or more chimeric genes are introduced into the variety or into a plant comprising all but 1, 2, 3, or more of the morphological and physiological characteristics (e.g., as listed in Table 1 and/or 2). Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into NUN 09194 TOF, or progeny of said variety, by transforming said variety or progeny of said variety with a transgene that confers the desired trait, wherein the transformed plant retains all or all but one, two or three of the phenotypic and/or morphological and/or physiological characteristics of NUN 09194 TOF or the progeny of said variety and contains the desired trait.

The disclosure also provides a plant or a cell of a plant comprising a desired trait produced by mutating a plant of variety NUN 09194 TOF or a cell thereof and selecting a plant the desired trait, wherein the mutated plant retains all or all but one of the phenotypic and morphological characteristics of said variety, optionally as described for each variety in Table 1 and/or 2, and contains the desired trait and wherein a representative sample of seed of variety NUN 09194 TOF to be deposited under Accession Number NCIMB 43588. In a further aspect, the desired trait is yield, storage properties, color, flavor, male sterility, herbicide tolerance, insect resistance, pest resistance, disease resistance, environmental stress tolerance, modified carbohydrate metabolism, modified protein metabolism or ripening or the mutation occurs in any of the following genes acs2, acs4, rin, pp2c1, arf9, intense, or myb12.

In one aspect, the disclosure provides a method for inducing mutation in NUN 09194 TOF comprising:
a. exposing a seed, a plant or a plant part or a cell of NUN 09194 TOF to a mutagenic compound or to radiation, wherein a representative sample of seed of NUN 09194 TOF is deposited under Accession Number NCIMB 43588.
b. selecting a seed, a plant or a plant part or a cell of NUN 09194 TOF having a mutation; and
c. optionally growing and/or multiplying the seed, plant or plant part or cell of NUN 09194 TOF having the mutation.

The disclosure also provides a plant having one, two or three physiological and/or morphological characteristics which are different from those of NUN 09194 TOF and which otherwise has all the physiological and morphological characteristics of said variety, wherein a representative sample of seed of variety NUN 09194 TOF will be deposited under Accession Number NCIMB 43588. In particular, variants which differ from NUN 09194 TOF in none, one, two or three of the characteristics mentioned in Table 1 and/or 2 are encompassed.

A part of NUN 09194 TOF (or of progeny of said variety or of a plant having all physiological and/or morphological characteristics but one, two or three which are different from those of said variety) encompasses any cells, tissues, organs obtainable from the seedlings or plants, such as but not limited to: a tomato fruit or a part thereof, a cutting, hypocotyl, cotyledon, seed coat, pollen and the like. Such parts can be stored and/or processed further. The disclosure further provides for food or feed products comprising a part of NUN 09194 TOF or a part of progeny of said variety, or a part of a plant having all but one, two or three physiological and/or morphological characteristics of NUN 09194 TOF, comprising one or more of such parts, optionally processed (such as canned, chopped, cooked, roasted, in a sauce, in a sandwich, pasted, puréed or concentrated, juiced, frozen, dried, pickled, or powdered).

In one aspect, the disclosure provides for a haploid plant and/or a doubled haploid plant of NUN 09194 TOF, or of a plant having all but one, two or three physiological and/or morphological characteristics of NUN 09194 TOF, or progeny of any of these. Haploid and doubled haploid (DH) plants can, for example, be produced by cell or tissue culture and chromosome doubling agents and regeneration into a whole plant. For example, DH production chromosome doubling may be induced using known methods, such as colchicine treatment or the like. In one aspect, the method comprises inducing a cell or tissue culture with a chromosome doubling agent, and regenerating the cells or tissues into a whole plant.

In yet another aspect, haploid plants and/or doubled haploid plants derived from NUN 09194 TOF that, when combined, make a set of parents of NUN 09194 TOF. The haploid plant and/or the doubled haploid plant of NUN 09194 TOF can be used in a method for generating parental lines of NUN 09194 TOF.

Using methods known in the art such as "reverse synthesis of breeding lines" or "reverse breeding", it is possible to produce parental lines for a hybrid plant such as NUN 09194 TOF. A skilled person can take any individual heterozygous plant (called a "phenotypically superior plant" in Example 2 of WO2014/076249 hereby incorporated by reference in its entirety; NUN 09194 TOF is such a plants) and generate a combination of parental lines (reverse breeding parental lines) that, when crossed, produce the variety NUN 09194 TOF. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014/076249 or from Wijnker et al., Nature Protocols Volume: 9, Pages: 761-772 (2014) DOI: doi:10.1038/nprot.2014.049, which are hereby incorporated by reference in their entireties. Thus, the disclosure provides a method for producing parental lines for a hybrid organism (e.g., NUN 09194 TOF), comprising: a) defining a set of genetic markers that are present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

The disclosure also provides a method for producing parental lines for hybrid NUN 09194 TOF comprising: genetically characterizing a doubled haploid line from NUN 09194 TOF to determine whether one or more genetic markers are present in a first homozygous form or in a second homozygous form in said line, wherein the one or more genetic markers are present in a heterozygous form in NUN 09194 TOF; and selecting at least one pair of doubled haploid lines that have complementary alleles for the one or more the genetic markers, wherein each member of the pair is suitable as a parental line for a hybrid organism, optionally this method further comprises defining a set of genetic markers present in a heterozygous form in NUN 09194 TOF; and producing doubled haploid lines from NUN 09194 TOF. Doubled haploid lines generated as described herein can be used in such a method.

Thus, in one aspect, the disclosure relates to a method of producing a combination of parental lines of a plant of NUN 09194 TOF comprising making doubled haploid cells comprising making doubled haploid cells from haploid cells from said plant or a seed of that plant; and optionally crossing these parental lines to produce and collecting seeds. In another aspect, the disclosure relates to a combination of parental lines produced by this method. In still another aspect, the combination of parental lines can be used to produce a seed or plant of NUN 09194 TOF when these parental lines are crossed. In still another aspect, the disclosure relates to a combination of parental lines from which a seed or plant having all physiological and/or morphological characteristics of NUN 09194 TOF (when the characteristics are determined at the 5% significance level for plants grown under the same conditions).

In another aspect, the disclosure comprises a method for making doubled haploid cells from haploid cells of NUN 09194 TOF comprises doubling cells of NUN 09194 TOF with a doubling agent, such as colchicine treatment.

In another aspect, the disclosure provides a method of introducing a single locus conversion or single trait conversion or a desired trait into NUN 09194 TOF comprising:
 a. obtaining a combination of a parental lines of NUN 09194 TOF, optionally through reverse synthesis of breeding lines;
 b. introducing a single locus conversion in at least one of the parents of step a; and
 c. crossing the converted parent with the other parent of step a) to obtain seed of NUN 09194 TOF.

A combination of a male and a female parental line of NUN 09194 TOF can be generated by methods described herein, for example, through reverse synthesis of breeding lines.

In another aspect, the disclosure provides a method of introducing a single locus conversion or single trait conversion or a desired trait into NUN 09194 TOF, comprising introducing a single locus conversion in at least one of the parents of NUN 09194 TOF; and crossing the converted parent with the other parent of NUN 09194 TOF to obtain seed of NUN 09194 TOF.

In another aspect, the step of introducing a single locus conversion in at least one of the parents comprises:
 i. obtaining a cell or tissue culture of cells of the parental line of NUN 09194 TOF;
 ii. genetically transforming or mutating said cells;
 iii. growing the cells into a plant; and
 iv. optionally selecting plants that contain the single locus conversion, the single trait conversion or the desired trait.

In another method, the step of introducing a single locus conversion in at least one of the parents comprises genetically transforming or mutating cells the parental line of NUN 09194 TOF; growing the cells into a plant; and optionally selecting plants that contain the single locus conversion, the single trait conversion or the desired trait.

In another embodiment, the step of introducing a single locus conversion in at least one of the parents comprises:
 i. crossing the parental line of NUN 09194 TOF with a second tomato plant comprising the single locus conversion, the single trait conversion or the desired trait;
 ii. selecting F1 progeny plants that contain the single locus conversion, the single trait conversion or the desired trait;
 iii. crossing said selected progeny plants of step ii with the parental line of step i, to produce a backcross progeny plant;
 iv. selecting backcross progeny plants comprising the single locus conversion, the single trait conversion or the desired trait and otherwise all or all but one, two or three of the morphological and physiological characteristics the parental line of step i to produce selected backcross progeny plants; and
 v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i) to produce selected backcross progeny plants, when grown in the same environmental conditions.

The disclosure further relates to plants obtained by this method.

In any of the above methods where the single locus conversion concerns a trait, the trait may be yield or pest resistance or disease resistance. In one aspect, the trait is disease resistance and the resistance is conferred to Tomato Mosaic Virus, Curly TOF Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), *Alternaria*, Bacterial Spot (*Xanthomonas vesicatoria*), Nematode (*Meloidogyne* spp), Late blight (*Phytophthora infestans* races), Leaf mold (*Cladosporium fulvum* races), Colorado potato beetle, Spider mites, or Whitefly and *Verticillium* Wilt (*Verticillium dahliae*). Other resistance genes, against pathogenic viruses, fungi, bacteria, nematodes, insects or other pests may also be introduced.

The disclosure also provides a combination of parental lines which, when crossed, produce a seed or plant having all physiological and/or morphological characteristics of NUN 09194 TOF but one, two or three which are different (when grown under the same environmental conditions), as well as a seed or plant having all physiological and/or morphological characteristics of NUN 09194 TOF, but one, two or three which are different (when the characteristics are determined at the 5% significance level for plants grown under the same conditions).

Also provided is a plant part obtainable from variety NUN 09194 TOF or from progeny of said variety or from a plant having all but one, two or three physiological and/or morphological characteristics which are different from those of NUN 09194 TOF, or from a vegetatively propagated plant of NUN 09194 TOF (or from its progeny or from a plant having all or all but one, two or three physiological and/or morphological characteristics which are different from those of NUN 09194 TOF), wherein the plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 09194 TOF, or hypocotyl, cotyledon, a scion, a stock, a rootstock, a pistil, an anther, or a flower or a part thereof.

In another aspect, the disclosure provides a method of determining the genotype of a plant disclosed herein comprising detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The disclosure also provides for a food or feed product comprising or consisting of a plant part described herein. Preferably, the plant part is a tomato fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable tomato fruits are generally sorted by size and quality after harvest. Alternatively the tomato fruits can be sorted by expected shelf life, pH or Brix.

NUN 09194 TOF may also be grown for use as rootstocks (stocks) or scions (cions). Typically, different types of tomatoes are grafted to enhance disease resistance, which is usually conferred by the rootstock, while retaining the horticultural qualities usually conferred by the scion. It is not uncommon for grafting to occur between cultivated tomato varieties and related tomato species. Methods of grafting and vegetative propagation are well-known in the art.

In another aspect, the disclosure provides to a plant comprising a rootstock or scion of NUN 09194 TOF.

All documents (e.g., patent publications) are herein incorporated by reference in their entirety, including the following cited references:

Acquaah, Principles of Plant Genetics and Breeding, 2007, Blackwell Publishing, ISBN-13: 978-1-4051-3646-4
Colijn-Hooymans (1994), Plant Cell, Tissue and Organ Culture 39: 211-217
Ince et al., (2010) Biochem. Genet. 48:83-95
Pisanu et al. ISHS 2004, Acta Hort. 660
Sang-Gu et al. (1988), Plant Cell, Tissue and Organ Culture 12: 67-74
Vidaysky and Czosnek, (1998) Phytopathology 88(9): 910-4
Vos et al. 1995, Nucleic Acid Research 23: 4407-4414
Wijnker et al., Nature Protocols Volume: 9, Pages: 761-772 (2014) DOI: 10.1038/nprot.2014.049
U.S. Pat. No. 4,822,949
U.S. Pat. No. 5,349,128
U.S. Pat. No. 5,492,827
U.S. Pat. No. 6,084,152
U.S. Pat. No. 6,765,130
WO2013/182646
WO2014/076249
WO2016/207432
WO2016/120438

EXAMPLES

Development of NUN 09194 TOF

The hybrid NUN 09194 TOF was developed from a male and female proprietary inbred line of Nunhems. The female and male parents were crossed to produce hybrid (F1) seeds of NUN 09194 TOF The seeds of NUN 09194 TOF can be grown to produce hybrid plants and parts thereof (e.g., tomato fruit). The hybrid NUN 09194 TOF can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 09194 TOF is uniform and stable.

Deposit Information

A total of 2500 seeds of the hybrid variety NUN 09194 TOF will be deposited according to the Budapest Treaty by Nunhems B.V. on Mar. 10, 2020, at the NCIMB Ltd., Ferguson Building, Craibstone Estate, Bucksburn, Aberdeen AB21 9YA, United Kingdom (NCIMB). The deposit will be assigned NCIMB number 43588. A deposit of NUN 09194 TOF and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 U.S.C. § 2321 et seq.).

The most similar variety to NUN 09194 TOF is referred to as Reference Variety, a variety from Seminis with the commercial name Merlice. Table 1 shows a comparison between NUN 09194 TOF and its Reference Variety based on a trial in the USA during the trial season 2018. Trial location Acampo, Calif., USA (38.192873 N 121232637). Seeded: May 9, 2017; transplanting date: Jun. 22, 2017; harvesting date: Sep. 25, 2017.

A trial of 40 plants of each variety, from which at least 15 plants or plant parts were randomly selected, were used to measure characteristics. For numerical characteristics, averages were calculated. For non-numerical characteristics, the type/degree was determined. Table 1 lists the USDA descriptors of NUN 09194 TOF and the Reference Variety (commercial variety).

In accordance with one aspect, the disclosure provides a plant having the physiological and morphological characteristics of NUN 09194 TOF as presented in Table 1.

TABLE 1

Objective Description of NUN 09194 TOF and its Reference Variety

| USDA Descriptor | NUN 09194 TOP | Merlice |
|---|---|---|
| Seedling: | | |
| Anthocyanin in hypocotyl of 2-15 cm: 1 = absent; 2 = present | n.r. | n.r. |
| habit of 3-4 week old seedling: 1 = normal; 2 = compact | n.r. | n.r. |
| Mature plant: | | |
| Height (cm) | 187.4 | 172.3 |
| Growth type: 1 = indeterminate; 2 = determinate | 1 | 1 |
| Form: 1 = lax; 2 = normal; 3 = compact; 4 = dwarf; 5 = brachytic | 2 | 2 |
| Size of canopy (compared to others of similar form) 1 = small; 2 = medium; 3 = large | 2 | 2 |
| Habit: 1 = sprawling; 2 = semi-erect; 3 = erect (Dwarf Champion) | 2 | 2 |
| Stem: | | |
| Branching: 1 = sparse (Brehm's Solid Red; Fireball); 2 = intermediate (Westover); 3 = profuse (UC 82) | 2 | 2 |
| Branching at cotyledon or first leafy node 1 = present; 2 = absent | 2 | 2 |
| Number of nodes before first inflorescence 1 = 1-4; 2 = 4-7; 3 = 7-10; 4 = 10 or more | 7.7 | 7.5 |
| Number of nodes between early (1st to 2nd, 2nd to 3rd) inflorescence 1 = 1-4; 2 = 4-7; 3 = 7-10; 4 = 10 or more | 3.2 | 3.8 |
| Pubescence on younger stems: 1 = smooth (no long hairs); 2 = sparsely hairy (scattered long hairs); 3 = moderately hairy; 4 = densely hairy or wooly | 1 | 2 |
| Leaf: | | |
| Type: 1 = tomato; 2 = potato (Trip-L-Crop) | 1 | 1 |
| Margins of major leaflets: 1 = absent; 2 = shallowly toothed or scalloped; 3 = deeply toothed or cut, sps. towards base | 2 | 2 |
| Marginal rolling or wiltiness: 1 = absent; 2 = slight; 3 = moderate; 4 = strong | 1 | 1 |
| Onset of leaflet rolling: 1 = early-season; 2 = mid-season; 3 = late-season | 3 | 3 |
| Surface of major leaflets: 1 = smooth; 2 = roguse (bumpy or veiny) | 1 | 1 |
| Pubescence: 1 = smooth (no long hairs); 2 = normal; 3 = hirsute; 4 = wooly | 1 | 2 |
| Inflorescence: | | |
| Type: 1 = simple; 2 = forked (2 major axes); 3 = compound (much branched) | 1 | 2 |
| Number of flowers in inflorescence average | 8.86 | 18.7 |
| Leafy or "running" inflorescence: 1 = absent; 2 = occasional; 3 = frequent | 2 | 2 |
| Flower: | | |
| Calyx: 1 = normal, lobes awl-shaped; 2 = macrocalyx, lobes large, leaflike; 3 = fleshy | 1 | 1 |
| Calyx-lobes: 1 = shorter the corolla; 2 = approx., equaling corolla; 3 = distinctly longer than corolla | 1 | 1 |
| Corolla color: 1 = yellow; 2 = old gold; 3 = white or tan | 1 | 1 |
| Style pubescence: 1 = absent; 2 = sparse; 3 = dense | 3 | 1 |
| Anthers: 1 = all fused into tube; 2 = separating into 2 or more groups at anthesis | 1 | 1 |
| Fasciation (1st flower of 2nd or 3rd inflorescence): 1 = absent; 2 = occasionally present; 3 = frequently present | 2 | 3 |
| Fruit: | | |
| Shape of transverse section: 1 = round; 2 = flattened; 3 = angular; 4 = irregular | 1 | 1 |
| Shape of stem end: 1 = flat; 2 = indented | 1 | 1 |
| Shape of blossom end: 1 = indented; 2 = flat; 3 = nippled; 4 = tapered | 2 | 1 |
| Shape of pistil scar: 1 = dot; 2 = stellate; 3 = linear; 4 = irregular | 1 | 2 |
| Abscission layer: 1 = present (pedicellate); 2 = absent (jointless) | 1 | 1 |
| Point of detachment of fruit at harvest 1 = at pedicel joint; 2 = at calyx attachment | 2 | 2 |
| Length of pedicel (from joint to calyx attachment) (mm) | 22.2 | 21.8 |
| Length of mature fruit (stem axis) (mm) | 45.34 | 39.98 |
| Diameter of fruit at widest point (mm) | 44.26 | 42.10 |
| Weight of mature fruit (gram) | 49.73 | 39.6 |
| Number of locules: 1 = two; 2 = three or four; 3 = five or more | 1 | 2 |
| Fruit surface: 1 = smooth; 2 = slightly rough; 3 = moderately rough or ribbed | 1 | 1 |
| Fruit base color (mature-green stage): 1 = light green (Lanal; VF 145-F5); 2 = light gray-green; 3 = apple or medium green (Heinz 1439 VF); 4 = yellow green; 5 = dark green | 4 (RHS N144A) | 3(RHS 144C) |
| Fruit pattern (mature-green stage): 1 = uniform green; 2 = green-shouldered; 3 = radial stripes on sides of fruit | 1 | 1 |
| Shoulder color if different from base: 1 = dark green; 2 = grey green; 3 = yellow green | n.r. | n.r. |
| Fruit color full ripe: 1 = white; 2 = yellow; 3 = orange; 4 = pink; 5 = red; 6 = brownish; 7 = greenish; 8 = other | 5 | 5 |
| Flesh color full ripe: 1 = yellow; 2 = pink; 3 = red/crimson; 4 = orange; 5 other | 3 (N34B) | 3 (N34A) |
| Flesh color: 1 = uniform; 2 = with lighter and darker areas in walls | 1 | 2 |
| Locular gel color of table-ripe fruit: 1 = green; 2 = yellow; 3 = red | 3 | 2 |
| Ripening: 1 = blossom to stem end; 2 = uniform | 1 | 1 |
| Ripening: 1 = inside out; 2 = uniformity; 3 = outside in | 2 | 2 |
| Stem scar size: 1 = small (Roma); 2 = medium (Rutgers); 3 = large | 1 | 1 |
| Core: 1 = coreless (absent or smaller than 6 × 6 mm); 2 = present | 1 | 1 |
| Epidermis color: 1 = colorless; 2 = yellow | 1 | 2 |
| Epidermis: 1 = normal; 2 = easy-peel | 1 | 1 |
| Epidermis texture: 1 = tender; 2 = average; 3 = tough | 2 | 2 |
| Thickness of pericarp (mm): | 4.6 | 4.6 |
| Chemistry and composition of full-ripe fruits: | | |
| pH | n.r. | n.r. |
| Titratable acidity as % citric | n.r. | n.r. |
| Total solids | n.r. | n.r. |
| Soluble solids as Brix | 7.54 | 7.4 |
| Phenology: | n.r. | n.r. |
| Seeding to 50% growth (1 open on 50% of plants) | n.r. | n.r. |
| Seed to once harvest | | |
| Fruit season: 1 = long (Marglobe); 2 = medium (Westover); 3 = short, concentrated (VF 145); 4 = very concentrated (UC82) | n.r. | n.r. |

TABLE 1-continued

Objective Description of NUN 09194 TOF and its Reference Variety

| USDA Descriptor | NUN 09194 TOF | Merlice |
|---|---|---|
| Relative maturity in areas tested:<br>1 = early; 2 = medium early; 3 =<br>medium; 4 = medium late; 5 = late; 6 = variable<br>Adaptation: | n.r. | n.r. |
| Culture: 1 = field; 2 = greenhouse | 2 | 2 |
| Principle use(s): 1 = home garden;<br>2 = fresh market; 3 = whole-pack canning;<br>4 = concentrated products 5 = other: Dice | 2 | 2 |
| Machine harvest: 1 = not adapted; 2 = adapted | 1 | 1 |
| Regions to which adaptation<br>has been demonstrated:<br>1 = Northeast; 2 = Mid Atlantic;<br>3 = Southeast; 4 Florida; 5 = Great<br>Plains, 6 = south central;<br>7 = Intermountain West; 8 =<br>Northwest; 9 = California<br>(Sacramento and Upper San Joaquin<br>Valley); 10 = California (Coastal Areas);<br>11 California (Southern<br>San Joaquin Valley & desserts) | n.r. | n.r. |

TABLE 2

| Non-USDA Descriptor | NUN 09194 TOF | Merlice |
|---|---|---|
| Stem: Length of internode after 2nd inflorescence | 234.5 | 207.7 |
| Leaf length (mm) | 29.2 | 30.10 |
| Leaf width (mm) | 22.8 | 23.70 |
| Leaf color (RHS chart value) | 137A | NN137B |
| Number of locules | 2.53 | 3.6 |

Table 1 and 2 contain typical values. Values may vary due to environment. Other values that are substantially equivalent are also within the scope of the disclosure. N.A.=not applicable; n.r.=not recorded.

What is claimed is:

1. A plant, plant part, or seed of tomato variety NUN 09194 TOF, wherein a representative sample of seed of said variety is deposited under Accession Number NCIMB 43588.

2. The plant part of claim 1, wherein said plant part is a leaf, pollen, an ovule, a fruit, a scion, a root, a rootstock, a cutting, a flower, or a cell.

3. A seed that produces the plant of claim 1.

4. A tomato plant having all of die physiological and morphological characteristics of the plant of claim 1.

5. A tissue or cell culture comprising regenerable cells of the plant of claim 1.

6. The tissue or cell culture according to claim 5, comprising cells or protoplasts derived from a plant part suitable for vegetative reproduction.

7. The tissue or cell culture according to claim 5, wherein the plant part is a meristem, a cotyledon, a hypocotyl, pollen, a leaf, an anther, a root, a root tip, a pistil, a petiole, a flower, a fruit, or a stem.

8. A tomato plant regenerated from the tissue or cell culture of claim 5, wherein the plant has all of the physiological and morphological characteristics of the plant of tomato variety NUN 09194 TOF, grown under the same environmental conditions, and wherein a representative sample of seed of tomato variety NUN 09194 TOF is deposited under Accession Number NCIMB 43588.

9. A method of producing the plant of claim 1, or a part thereof, said method comprising vegetative propagating of at least a part of the plant of variety NUN 09194 TOF, wherein a representative sample of seed of said variety is deposited under Accession Number NCIMB 43588.

10. The method of claim 9, wherein said vegetative propagating comprises regenerating a whole plant from said part of the plant of variety NUN 09194 TOF, wherein a representative sample of seed of said variety is deposited under Accession Number NCIMB 43588.

11. The method of claim 9, wherein said part is a cutting, a cell culture or a tissue culture.

12. A vegetative propagated plant, or a part thereof produced by the method of claim 9, wherein the vegetative propagated plant and part thereof have all of the physiological and morphological characteristics of the plant of variety NUN 09194 TOF, grown under the same environmental conditions, and wherein a representative sample of seed of tomato variety NUN 09194 TOF is deposited under Accession Number NCIMB 43588.

13. A method of producing a tomato seed, said method comprising crossing the plant of claim 1 with a second tomato plant at least once, selecting a progeny tomato plant from said crossing and allowing the progeny tomato plant to form seed.

14. A tomato plant having all the physiological and morphological characteristics of the plant of claim 1, when grown under the same environmental conditions, wherein a representative sample of seed of tomato variety NUN 09194 TOF is deposited under Accession Number NCIMB 43588, further comprising a transgene.

15. A method of producing doubled haploids of tomato variety NUN 09194 TOF, said method comprising making doubled haploid cells from haploid cells of the plant or plant part of claim 1, wherein a representative sample of seed of tomato variety NUN 09194 TOF is deposited under Accession Number NCIMB 43588.

16. A plant comprising the scion or rootstock of claim 2.

17. A container comprising the plant, plant part or seed of claim 1.

18. A method of producing a tomato fruit, said method comprising growing the plant of claim 1 until it sets at least one fruit, and collecting the fruit.

19. A method for collecting pollen of tomato variety NUN 09194 TOF, said method comprising growing the plant of claim 1 until at least one flower contains pollen, and collecting the pollen.

20. A plant of tomato variety NUN 09194 TOF having all of the physiological and morphological characteristics of the plant of claim 1, wherein a representative sample of seed of said variety is deposited under Accession Number NCIMB 43588, when grown under the same environmental conditions, further comprising a single locus conversion, wherein the single locus conversion confers male sterility, herbicide tolerance, insect resistance, pest resistance, disease resistance, environmental stress tolerance, modified carbohydrate metabolism, or modified protein metabolism.

21. A method of producing a modified tomato plant having a single trait, said method comprising mutating a tomato plant or plant part of tomato variety NUN 09194 TOF, wherein a representative sample of seed of said tomato variety is deposited under Accession Number NCIMB 43588 , and wherein the modified plant otherwise has all of the physiological and morphological characteristics of the plant of variety NUN 09194 TOF and the single trait.

22. A method of determining the genotype of the plant of claim 1, said method comprising obtaining a sample of nucleic acids from said plant and detecting in said nucleic acids a plurality of polymorphisms, thereby determining the genotype of the plant and storing the results of detecting the plurality of polymorphisms on a computer readable medium.

* * * * *

UNITED STATES PATENT AND TRADEMARK OFFICE
CERTIFICATE OF CORRECTION

PATENT NO. : 10,709,102 B2
APPLICATION NO. : 15/995874
DATED : July 14, 2020
INVENTOR(S) : Bernard Catharina Hubert Silvertand It is certified that error appears in the above-identified patent and that said Letters Patent is hereby corrected as shown below:

In the Claims

Claim 4, Column 25, Line 50, reads "die", should read --the--

Signed and Sealed this
First Day of September, 2020

Andrei Iancu
*Director of the United States Patent and Trademark Office*